United States Patent [19]

Covey et al.

[11] Patent Number: 4,707,491
[45] Date of Patent: Nov. 17, 1987

[54] ANTICONVULSANT γ-THIOBUTYROLACTONE DERIVATIVES

[75] Inventors: Douglas F. Covey; Jeffrey A. Levine; James A. Ferrendelli, all of St. Louis, Mo.

[73] Assignee: Washington University, St. Louis, Mo.

[21] Appl. No.: 811,919

[22] Filed: Dec. 20, 1985

[51] Int. Cl.$^4$ .................... A61K 31/38; C07D 333/32
[52] U.S. Cl. ........................................ 514/445; 549/62
[58] Field of Search .......................... 549/62; 514/445

[56] References Cited

U.S. PATENT DOCUMENTS 3,488,732 1/1970 Heiba .................................... 549/62

OTHER PUBLICATIONS

Klunk et al., Molecular Pharmacol. 22, 438–443, (1982).
Ferrendelli et al., Chem. Absts. 100: 9652b, (1984).
Klunk et al., Chem. Absts. 99:20579, (1983).
Klunk et al., Chem. Absts. 99: 17607, (1983).
Kendall and Wells, Chem. Absts, 81: 151465, (1974).
Gorski et al., Tetrahedron Lett. No. 30, pp. 2577–2580, (1976).
Stevens et al., J. Org. Chem. 19, pp. 1996–2003, (1954).
Overberger et al., J. Org. Chem. 27, pp. 3539–3545, (1962).
Tamaru et al., J. Amer. Chem. Soc. 106(4), pp. 1079–1085, (1984).
Bass et al., Tetrahedron 22(1), pp. 285–291, (1966).
Korte et al., Chem. Ber. 94, 1966–1976, (1961).
Aboul-Enein et al., Chem. Absts. 94: 103290.

Primary Examiner—Alan Siegel
Attorney, Agent, or Firm—Scott J. Meyer; James W. Williams, Jr.

[57] ABSTRACT

γ-Thiobutyrolactone derivatives having short chain α- and/or γ-alkyl or alkenyl substituents have useful anticonvulsant properties.

7 Claims, No Drawings

ANTICONVULSANT γ-THIOBUTYROLACTONE DERIVATIVES

BACKGROUND OF THE INVENTION

This invention relates to γ-thiobutyrolactone derivatives having useful anticonvulsant activity and, more particularly, to α- and/or γ-substituted γ-thiobutyrolactones.

Convulsant seizures are manifested in various chronic central nervous system (CNS) disorders, particularly epilepsies. These seizures are generally correlated with abnormal and excessive EEG discharges. A variety of drugs have been used for treatment of these seizures. Many of the older drugs are structurally related to phenobarbital, for example, the hydantoins, the deoxybarbiturates, the oxazolidinediones and the succinimides. More recently developed anticonvulsant compounds include the benzodiazepines, iminostilbenes and valproic acid.

Recently, several analogs of γ-butyrolactone were synthesized and tested for their behavioral and electrophysiologic actions. It was found that those analogs substituted in the alpha position or in both the alpha and gamma positions and devoid of beta substituents were anticonvulsant and were inhibitory in the brain. Klunk, Covey and Ferrendelli, *Mol. Pharmacol.* 22(2), 438–443 (1982). By way of comparison, those analogs having substitutions in the beta position or in both the alpha and beta position were found to be convulsive compounds that were excitatory in brain tissue, in vivo and in vitro. Ibid., pp. 431–437. Studies of the structure-activity relationships of these compounds led to the development of a hypothetical molecular model explaining the convulsant and anticonvulsant properties of alkyl-substituted γ-butyrolactones.

BRIEF DESCRIPTION OF THE INVENTION

In accordance with the present invention it has been found that certain γ-thiobutyrolactone derivatives have useful anti-convulsant activity. These compounds can be represented by the following structural formula:

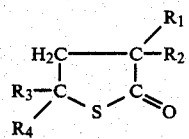

wherein
$R_1$ = H, alkyl or alkenyl having from 1 to about 4 carbon atoms,
$R_2$ = H, alkyl or alkenyl having from 1 to about 4 carbon atoms,
$R_3$ = H, alkyl or alkenyl having from 1 to about 4 carbon atoms,
$R_4$ = H, alkyl or alkenyl having from 1 to about 4 carbon atoms,
and in which at least one of $R_1$, $R_2$, $R_3$ or $R_4$ is not H.

Those compounds of the above structural formula having two dissimilar α-alkyl or α-alkenyl substituents ($R_1$ and $R_2$) are novel compounds.

The alkyl substituents in the above structural formula are illustrated by methyl, ethyl, propyl, isopropyl, sec-butyl and tert-butyl groups. The alkenyl substituents are illustrated by allyl and isopropenyl. Representative compounds with these substituents thus are for example:

α-methyl-γ-thiobutyrolactone;
α-ethyl-γ-thiobutyrolactone;
α-propyl-γ-thiobutyrolactone;
α-isopropyl-γ-thiobutyrolactone;
α-t-butyl-γ-thiobutyrolactone;
α-α-dimethyl-γ-thiobutyrolactone;
α-ethyl-α-methyl-γ-thiobutyrolactone;
α-ethyl-α-propyl-γ-thiobutyrolactone;
α-methyl-α-propyl-γ-thiobutyrolactone;
α-isopropyl-α-methyl-γ-thiobutyrolactone;
α-t-butyl-α-methyl-γ-thiobutyrolactone;
α-allyl-γ-thiobutyrolactone;
α-isopropenyl-γ-thiobutyrolactone;
α-γ-diethyl-α-γ-dimethyl-γ-thiobutyrolactone; and
γ-ethyl-γ-methyl-γ-thiobutyrolactone.

Preferred compounds in the foregoing class of compounds are α-ethyl-α-methyl-γ-thiobutyrolactone (α-EMTBL) and α-isopropyl-γ-thiobutyrolactone.

DETAILED DESCRIPTION OF THE INVENTION

The γ-thiobutyrolactone derivatives of this invention can be prepared by various means. They are readily prepared by converting the α- and/or γ-substituted-γ-butyrolactones to the corresponding α- and/or γ-substituted-γ-thiobutyrolactones. Thus, the α- and/or γ-substituted-γ-butyrolactones can be reacted with a reagent for inserting a sulfur atom into the ring in place of the oxygen atom. A suitable such thio introducing reagent is, for example, potassium thiolacetate (potassium thioacetate). Preferably, the α- and/or γ-substituted-γ-butyrolactone is reacted with the potassium thioacetate in organic solvent medium at elevated temperature. The reaction thus proceeds well in high boiling solvents such as, for example, N,N-dimethylacetamide (DMA), which has a bp$_{760}$ 163°–165°, or N,N-dimethylformamide (DMF), which has a bp$_{760}$ 153°. In DMA, the preferred reaction temperature is from about 150° C. to about 160° C., which is slightly below the solvent boiling point. A general procedure for converting lactones to thiolactones using potassium thioacetate in high boiling solvents is described by Gerecke et al., *Helv. Chim. Acta* 53, 991–999 (1970).

Starting materials for use in the above reaction are known. For example, α-isopropyl-γ-butyrolactone is described by Kendall and Wells, *Aust. J. Chem.* 27 (10), 2293–2295 (1974). Klunk et al., *Mol. Pharmacol.* 22(2), 438–443 (1982), describe α-ethyl-α-methyl-γ-butyrolactone, α,α-dimethyl-γ-butyrolactone and α-isopropylidene-γ-butyrolactone.

Several of the γ-thiobutyrolactone derivatives used in the present invention are known organic compounds. Thus, Gorski et. al., *Tetrahedron Lett.* No. 30, 2577–2580 (1976), describe α-methyl-γ-thiobutyrolactone and α-n-butyl-γ-thiobutyrolactone; Aboul-Enein, *Pharm. Acta Helv.* 55(9), 228–30 (1980), disclose α-ethyl-γ-thiobutyrolactone; Baas et al., *Tetrahedron* 22(1), 285–291 (1966), teach α,α-dimethyl-γ-thiobutyrolactone; Stevens and Tarbell, *J. Org. Chem.* 19, 1996–2003 (1954), describe γ-methyl-γ-thiobutyrolactone and γ,γ-dimethyl-γ-thiobutyrolactone; Korte and Christoph, *Chem. Ber.* 94, 1966–1976 (1961), disclose γ-methyl-γ-thiobutyrolactone, γ-isopropyl-γ-thiobutyrolactone and γ-isopropyl-γ-methyl-γ-thiobutyrolactone; Overberger and Ferraro, *J. Org. Chem.* 27, 3539–3545 (1962), teach α,α,γ-trimethyl-γ-thiobutyrolactone; and Tamaru et al., *J. Am. Chem. Soc.* 106(4), 1079–1085 (1984), describe α-γ-dimethyl-γ-thiobutyrolactone.

However, none of these γ-thiobutyrolactone derivatives were previously known as or suggested to be active anticonvulsant agents. The α-alkyl substituents in these previously known compounds are the same in any given compound.

Another method for preparing the compounds of this invention comprises the α-alkylation or γ-alkylation of γ-thiobutyrolactone (4-butyrothiolactone). The latter compound is a commercially available reagent having the structure:

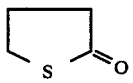

The alkylating reagent should be selected such as to provide the alkyl or alkenyl groups described hereinbefore on the alpha and/or gamma position in the γ-thiobutyrolactone. See Gorski et al., surpa, for a general procedure for alkylating γ-thiobutyrolactone.

The compounds of this invention also can be prepared by ring closure following insertion of a sulfur atom into the acyclic precursor of the ring compound. Thus, Lumma et al., *J. Org. Chem.* 35(10), 3442 (1970), describe a general method in which the γ-butyrolactone is treated with benzyl mercaptide anion to yield the 4-(benzythio)butyric acid which, on treatment with trifluoric anhydride, cyclizes to give the γ-thiobutyrolactone. This general method can be adapted to analogously produce the α- and/or γ-substituted γ-thiobutyrolactones.

The anticonvulsant activity of the γ-thiobutyrolactone derivatives of this invention can be demonstrated by various laboratory tests commonly used for candidate anticonvulsant drugs. One recognized test which is frequently used for this purpose is to determine the capacity of the drug to modify the effects of maximal electric shock (MES) by inhibition of tonic hindlimb extension. See, for example, the test described by Swinyard and co-workers at *J. Pharmacol. Exper. Therap.* 106, 319–330 (1952).

Another acceptable test for demonstrating anticonvulsant activity involves measurement of the candidate drug's capacity to elevate the dose of pentylenetetrazol required to precipitate tonic-clonic convulsions. See, for example, Krall et al., *Epilepsia* 19, 409–428 (1978).

The surprising and unexpected advantages of the γ-thiobutyrolactone derivatives of this invention are illustrated by the above conventional anticonvulsant tests of a preferred compound of this invention, namely α-ethyl-α-methyl-γ-thiobutyrolactone:

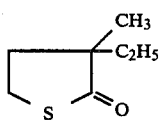

in comparison with known structural analogs having anticonvulsant activity, namely α-ethyl-α-methyl-γ-butyrolactone (α-EMBL) and ethosuximide:

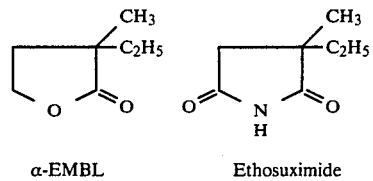

α-EMBL      Ethosuximide

In mice, the preferred α-ethyl-α-methyl-γ-thiobutyrolactone (α-EMTBL) protects against pentylenetetrazol (PTZ) seizures and has an ED50 of about 80 mg/kg. In addition, it is able to protect mice against maximal electroshock seizures (MES) and has an ED50 of about 230 mg/kg. Tests for acute toxicity using the rotorod test show that the compound has a TD50 in mice of about 350 mg/kg. Thus, the compound can protect against both PTZ and MES seizures at nontoxic doses. The rotorod test is a standard method used in mice to access neurotoxicity and is described, for example, by Krall et al., *Epilepsia* 19, 409–428 (1978).

Comparison of the anticonvulsant profile of α-ethyl-α-methyl-γ-thiobutyrolactone (α-EMTBL) with α-EMBL, ethosuximide and valproic acid shows α-EMBTL to be more potent than the other compounds against PTZ seizures. Both valproic acid and α-EMTBL have anti-MES activity, but ethosuximide and α-EMBL do not. The therapeutic index TD50/ED50 of all four compounds is substantially similar. Thus, α-EMTBL is a more potent anticonvulsant compound than ethosuximide, valproic acid or α-EMBL, and, similar to valproic acid, has a broader spectrum of action than ethosuximide or α-EMBL. The advantage of α-EMTBL over the structural analogs, α-EMBL or ethosuximide, and over the important antiepileptic drug—valproic acid—is evident from the above.

The following examples will further illustrate the invention in greater detail although it will be understood that the invention is not limited to these specific examples. Examples 1 to 6 and 13 are based on work actually done while Examples 7 to 12 are reasonably extrapolated from the work carried out in the former Examples.

EXAMPLE 1

α-Ethyl-α-methyl-γ-thiolbutyrolactone

Utilizing a general method described by Gerecke et al., *Helv. Chim. Acta* 53, 991 (1970), a mixture of 8.90 g (69.4 mmol) of α-ethyl-α-methyl-γ-butyrolactone and 12.4 g (109 mmol) of potassium thiolacetate in 50 mL of N,N-dimethylacetamide (DMA) was heated at 150°–160° C. with stirring for 4 hours. The dark brown mixture was partitioned between hexanes (200 mL) and water (200 mL). The aqueous phase was further extracted with two 100 mL portions of hexanes. The combined organic extract was washed with 100 mL of water followed by 50 mL of satd. NaCl, then dried over $Na_2SO_4$. The solvent was removed to leave a red oil. Vacuum distillation yielded 7.80 g (78%) of α-ethyl-α-methyl-γ-thiolobutyrolactone as a colorless liquid: bp 59–61/0.5 torr; $^1$H-nmr (CDCl$_3$, Me$_4$Si)δ3.31 (t,2, J=6 Hz, γ-CH$_2$), 2.4–1.8 (m, 2, β-CH$_2$), 1.8–1.3 (m, 2, CH$_2$CH$_3$), 1.11 (S, 3, CH$_3$), 0.88 ppm (t, 3, J=6 Hz, CH$_2$CH$_3$); IR (neat) 1700 cm$^{-1}$ (C=O, thiolester); UV (95% EtOH)λ$_{max}$249 nm (ε=470). A second distillation yielded an analytical sample.

Anal. Calcd. for $C_7H_{12}OS$: C, 58.29; H, 8.39; S, 22.23, Found: C, 58.48; H, 8.55; S, 22.28.

EXAMPLE 2

α-Isopropylidene-γ-butyrolactone

According to the method of Minami et al., *J. Org. Chem.* 39, 3236–3238 (1975), the carbanion of 60.0 g (27.0 mmol) of α-(O, Odiethyl-phosphono)-γ-butyrolactone was prepared by treatment with 6.5 g (27 mmol) of NaH in 50 mL of dry benzene at 50°–60° C. Addition of 3.0 mL (2.4 g; 41 mmol) of dry acetone, followed by stirring at 50°–60° C. for 16 h, yielded a clear yellow solution, with a viscous oil at the bottom of the vessel. The solution was decanted and the vessel rinsed with two 100-mL portions of 2% aqueous HCl followed by 50-mL of benzene. All the liquids were combined and the phases were separated. The aqueous phase was further extracted with two 50-mL portions of benzene and the combined organic extracts were washed with 50 mL of 2% HCl, 50 mL of $H_2O$, 50 mL of 5% $NaHCO_3$, and 25 mL of satd. NaCl, then dried over $Na_2SO_4$. The solvent was removed to leave an orange oil which, on distillation, yielded 27.1 g (80%) of α-isopropylidene-γ-butyrolactone which was identical with material prepared by Klunk et al., *Mol. Pharm.* 22, 438–443 (1982).

EXAMPLE 3

α-Isopropyl-γ-butyrolactone

A mixture of 8.3 g (66 mmol) of α-isopropylidene-γ-butyrolactone and 0.5 g of 10% Pd-C in 200 mL of EtOAc was hydrogenated at 40 p.s.i. in a Parr shaker until $H_2$ uptake ceased (ca. 1 h). The catalyst was removed by filtration through Celite, the solvent removed, and the product distilled to yield 7.8 (93%) of α-isopropyl-γ-butyrolactone as a colorless liquid: bp 53°–54° C./0.2–0.3 torr. The $^1$H-nmr and IR were identical to those reported by Kendall and Wells, *Aust. J. Chem.* 27(10), 2293–2295 (1974).

EXAMPLE 4

α-Isopropyl-γ-thiolobutyrolactone was prepared by treating 958 mg (7.47 mmol) of α-isopropyl-γ-butyrolactone with 1.296 g (8.99 mmol) of potassium thiolacetate in 5 mL DMA for 2 h at 150°–160° C. The mixture was partitioned between hexanes (50 mL) and water (50 mL), the aqueous phase further extracted with two 25 mL portions of hexanes, and the combined organic extract was washed with 50 mL of water followed by 25 mL of satd. NaCl. The solution was dried over $Na_2SO_4$ and the solvent removed. Bulb-to-bulb distillation (pot temp. 70° C./0.2–0.3 torr) gave a pale yellow liquid. Chromatography on silica gel (hexane/EtOAc; 19/1 followed by bulb-to-bulb distillation (pot temp. 55° C./0.2–0.3 torr) yielded 616 mg (57%) of α-isopropyl-γ-thiolobutyrolactone as a colorless liquid: $^1$H-nmr (CDCl$_3$, Me$_4$Si)δ3.4–3.2 (m, 2, γ-CH$_2$), 2.7–1.9 (m, 4, α-CH, β-CH$_2$, and CH(CH$_3$)$_2$), 1.03 (d, 3, J=7 Hz, CH$_3$), 0.91 ppm (d, 3, J=7 Hz, CH$_3$); IR (neat) 1700 cm$^{-1}$ (C=O, thiolester); UV (95% EtOH)λ$_{max}$251 nm (ε=570).

Anal. Calcd. for $C_7H_{12}OS$: C, 58.29; H, 8.39; S, 22.23. Found: C, 58.47; H, 8.74, S, 21.95.

EXAMPLE 5

α,α-Di-isopropyl-γ-butyrolactone

A solution of isopropylcyclohexylamide was prepared by treating 8.01 g (56.7 mmol) of isopropylcyclohexylamine in 50 mL of dry tetrahydrofuran (THF) with 24 mL (57.6 mmol) of 2.4 M n-butyllithium in hexane at 0° C. in an inert atmosphere. The solution was cooled to −78° C. and a solution of 6.04 g (47.2 mmol) of α-isopropyl-γ-butyrolactone in 200 mL of dry THF was added dropwise. The mixture was stirred at −78° C. for 45 min, then 8.83 g (51.9 mmol) of 2-iodopropane and 5.1 mL of hexamethylphosphoramide (HMPA) was added all at once. The reaction mixture was stirred at −40° C. for 4 h, then at −20° C. for 15 h. The reaction was quenched by addition of 100 mL of 1N HCl followed by 100 mL of hexanes. The layers were separated and the aqueous phase was further extracted with two 100 mL portions of hexanes. The combined organic extract was washed with water, 5% $NaHCO_3$, 5% $Na_2S_2O_3$, water, and salt NaCl, then dried over $Na_2SO_4$. The solvent was removed and the residue distilled (55° C./0.1 torr) to give impure α-α-di-isopropyl-γ-butyrolactone as a colorless liquid which was then purified by HPLC (silica gel; 5% acetone in hexane) to yield 1.08 g (13.4%) of pure material: $^1$H-nmr (CDCl$_3$, Me$_4$Si)δ4.22 (t, 2, J=8 Hz, γ-CH$_2$), 2.4–1.8 (m, 4, β-CH$_2$ and CH(CH$_3$)$_2$), 0.99 (d, 6, J=7 Hz, CH$_3$), 0.94 ppm (d, 6, J=7 Hz, CH$_3$); IR (neat) 1760 cm$^{-1}$ (C=O, γ-lactone).

Anal. Calcd. for $C_{10}H_{18}O_2$: C, 70.55; H, 10.66. Found: C, 70.74; H, 10.37.

EXAMPLE 6

α,α-Di-isopropyl-γ-thiolobutyrolactone was prepared by treating 459 mg (2.70 mmol) of α,α-di-isopropyl-γ-butyrolactone with 756 mg (6.62 mmol) of potassium thiolacetate in 5 mL of DMA for 24 h at 150°–160° C. with stirring. After working up with hexanes and water as described above, the product was purified first by chromatography on silica gel (hexane/EtOAc; 19/1), then by HPLC (silica gel; 50% benzene in hexanes). The major fraction was collected, the solvent removed, and the material was distilled bulb-to-bulb (pot temp. 55°–60° C./0.2–0.3 torr) to give a colorless liquid. Purification by HPLC (silica gel; 2.5% EtOAc in hexanes) yielded 40 mg (8.0%) of α-α-di-isopropyl-γ-thiobutyrolactone as a colorless liquid: $^1$H-nmr (CDCl$_3$, Me$_4$Si)δ3.32 (t, 2, J=7 Hz, γ-CH$_2$), 2.25 (t, 2, J=7 Hz, β-CH$_2$), 2.4–1.9 (m, 2, CH(CH$_3$)$_2$), 0.99 ppm (d, 12, J=7 Hz, CH$_3$); IR (neat) 1700 cm$^{-1}$ (C=O, thiolester); UV (95% EtOH) λ$_{max}$251 nm (ε=550).

Anal. Calcd. for $C_1H_{18}OS$: C, 64.47; H, 9.74; S, 17.21. Found: C, 64.79; H, 9.71; S, 17.20.

EXAMPLE 7

α-t-Butyl-γ-butyrolactone

A solution of lithium di-isopropylamide, prepared by addition of 8.33 mL (20 mmol) of 2.4 M n-butyllithium in hexane to a 0° C. solution of 3.40 g (20 mmol) of di-isopropylamine in 50 mL of dry THF, is cooled to −78° C. and to it is added dropwise over 30 min a solution of 2.60 g (20 mmol) of methyl t-butylacetate in 50 mL of dry THF. The mixture is stirred at −78° C. for 1 h, then 18.8 g (100 mmol) of 1,2-dibromoethane and 10 mL of HMPA is added all at once. The mixture is stirred for 4 h at −78° C., then allowed to warm slowly to room temperature. Water (100 mL) is carefully added, and the mixture is then extracted with three 100-mL portions of hexane. The combined organic extract is washed with water (100 mL) then with satd. NaCl (50 mL) and dried over $Na_2SO_4$. The solvent is removed and the product, methyl 2-t-butyl-4-bromobutyrate, is purified by vacuum distillation. The ester is hydrolyzed by refluxing for 2 h with 25 mL (50 mmol) of 2 N NaOH, the water is removed in Vacuo, and the residue is suspended in 25 ml of di-n-butylphthalate in a 200 mL round-bottomed flask with an efficient stirrer, connected to a distillation apparatus, and heated slowly under vacuum (0.5 torr) in an oil bath to 180° C. with vigorous stirring. The distillate is collected and the reaction is terminated when di-n-butylphthalate begins to reflux in the still head. The product, α-t-butyl-γ-butyrolactone, is then purified by vacuum distillation.

EXAMPLE 8

α-t-Butyl-γ-thiolobutyrolactone

A mixture of 1.42 g (10 mmol) of α-t-butyl-γ-butyrolactone and 1.7 g (15 mmol) of potassium thiolactate in 10 mL of DMA is heated at 150°–160° C. for 4 h. The mixture is partitioned between hexane (50 mL) and water (50 mL). The hexane phase is washed with water then with satd. NaCl and dried over $Na_2SO_4$. The solvent is removed and the residue is distilled in vacuo to yield α-t-butyl-γ-thiolbutyrolactone.

EXAMPLE 9

α,α-Di-t-butyl-γ-butyrolactone

A solution of 1.42 g (10 mmol) of α-t-butyl-γ-butyrolactone in 25 mL of dry THF is added dropwise over 20 min to a −78° C. solution of 10 mmol of lithium di-isopropylamide in 25 mL of THF (prepared as above), and the mixture stirred for 1 h at −78° C. Chlorotrimethylsilane (1.3 g; 12 mmol) is added all at once, the mixture stirred for 1 h at −78° C., allowed to warm slowly to room temperature, then poured into 100 mL of hexanes. The mixture is washed with 50 mL of cold water, 25 mL of satd. NaCl, and dried over $Na_2SO_4$. The solvent is removed and the trimethylsilyl enolate of α-t-butyl-γ-butyrolactone is isolated by vacuum distillation. As described by Reetz and Schwellnus, *Tetrahedron Lett.* No. 17, 1455–1458 (1978), the silyl enolate is dissolved in 10 mL of dry $CH_2Cl_2$ and treated with 2.7 g (30 mmol) of t-butylchloride and a catalytic amount (ca. 50 mg) of $ZnCl_2$ for 24 h at room temperature. To the mixture is added 30 mL of cold 5% $NaHCO_3$ and it is then extracted with four 15 mL portions of water and dried over $MgSO_4$. SThe solvent is removed and the product, α-α-di-t-butyl-γ-butyrolactone, is purified by vacuum distillation.

EXAMPLE 10

α,α-Di-t-butyl-γ-thiolobutyrolactone

A mixture of 1.0 g (5 mmol) of α,α-di-t-butyl-γ-butyrolactone and 2.3 g (20 mmol) of potassium thiolacetate in 5 mL DMA is heated at 150°–160° C. for 18 h. The mixture is partitioned between 25 mL of hexane and 25 mL of water, the hexane phase is washed with water, then with satd. NaCl and dried over $Na_2SO_4$. The solvent is removed and the residue is distilled bulb-to-bulb (pot temp. 70° C./0.2 torr) to yield impure α,α-di-t-butyl-γ-thiolobutyrolactone, which is then purified by HPLC (silica gel; 2.5% EtOAc in hexane).

EXAMPLE 11

γ-Ethyl-γ-methyl-γ-thiolobutyrolactone

A mixture of 1.54 g (12 mmol) of γ-ethyl-γ-methyl-γ-butyrolactone and 2.8 g (24 mmol) of potassium thiolacetate in 10 mL of DMA is heated at 150°–160° C. for 4 h. The mixture is partitioned between 100 mL of hexane and 100 mL of water and the organic phase is washed with water followed by saturated NaCl, then dried over $Na_2SO_4$. The solvent is removed by evaporation and the residue distilled in vacuo to yield γ-ethyl-γ-methyl-γ-thiolobutyrolactone.

EXAMPLE 12

α,γ-Diethyl-α,γ-dimethyl-γ-thiobutyrolactone

A mixture of 1.10 g (5.9 mmol) of α-γ-diethyl-α-γ-dimethyl-γ-butyrolactone and 1.66 g (14.6 mmol) of potassium thiolacetate in 5 mL of DMA is heated at 150°–160° C. for 4 h. The mixture is partitioned between 50 mL of hexane and 50 mL of water and the organic phase is washed with water followed by saturated NaCl, then dried over $Na_2SO_4$. The solvent is removed by evaporation and the residue distilled in vacuo to yield α,γ-diethyl-α,γ-dimethyl-γ-thiobutyrolactone.

EXAMPLE 13

Compounds were tested for anticonvulsant activity and toxicity in mice by the following tests.

ANTICONVULSANT TESTS

Pentylenetetrazol Seizure Threshold Test

Pentylenetetrazol (85 mg/kg; CD97 or 100 mg/kg; CD100) is injected IP into mice in a volume of 0.01 ml/g body weight. The animals are placed in isolation cages and observed for the next 30 min. for the presence or absence of a seizure. A threshold convulsion is defined as one episode of clonic spasms that persists for at least a 5-sec period. Absence of a threshold convulsion during the 30 min. period of observation is taken as the endpoint and indicates that the substance has the ability to elevate the threshold of the pentylenetetrazol seizure.

Maximal Electroshock Seizure Test

At the time of peak effect of the test substance, a drop of 0.9% sodium chloride is applied to the eyes of each animal. Corneal electrodes are applied to the eyes, and an electrical stimulus of 50 mA is delivered for 0.2 sec. The animals are held by hand and released at the time of stimulation for observation of the seizure. Abolition of the hindleg tonic extension component is taken as the endpoint for this test. The tonic component is considered abolished if the hindleg tonic extension does not exceed 90° with the plane of the body.

Rotorod Test for Toxicity

This test is used in mice to assess neurotoxicity. Mice are placed on the rotorod, which rotates at 6 rpm, and tested for maintenance of their equilibrium for 10 min. All mice are pre-tested before test substance is given. At the time of peak effect of the test substance, mice are put back on the rotorod for 10 min. Neurological deficit (toxicity) is indicated by the inability of the animal to maintain its equilibrium for 10 min. on this rotating rod.

The anticonvulsant properties of α-ethyl-α-methyl-γ-thiobutyrolactone (α-EMTBL) were determined in mice by the foregoing tests. This compound protected against clonic seizures produced by 85 mg/kg pentylenetetrazol (ED50=131 mg/kg). When tested against 100 mg/kg pentylenetetrazol it prevented clonic seizures (ED50=143 mg/kg) and tonic seizures (ED50=85 mg/kg). In addition, it was able to protect mice against maximal electroshock seizures and had an ED50 of approximately 230 mg/kg. Tests for acute toxicity revealed α-EMTBL had a TD50 of approximately 350 mg/kg. Thus, α-EMTBL protects against both pentylenetetrazol seizures and maximal electroshock seizures at non-toxic doses.

In comparison, α-ethyl-α-methyl-γ-butyrolactone (α-EMBL) protected against clonic seizures produced by 85 mg/kg pentylenetetrazol with an ED50 of 226 mg/kg; against clonic seizures produced by 100 mg/kg pentylenetetrazol with an ED50 of 304; and against tonic seizures produced by 100 mg/kg pentylenetetrazol with an ED50 of 250 mg/kg. No protection against maximal electroshock seizures by α-EMBL was observed at doses up to 350 mg/kg. The TD50 for α-EMBL (rotorod test) was approximately 350 mg/kg. Thus, α-EMBL protects only against pentylenetetrazol seizures at non-toxic doses.

In summary, α-EMTBL is both a more potent anticonvulsant and has a broader spectrum of action than α-EMBL.

α-isopropyl-γ-thiobutyrolactone was also tested against 85 mg/kg pentylenetetrazol and maximal electroshock. It blocked pentylenetetrazol seizures (ED50-137 mg/kg) and maximal electroshock seizures (ED50-240 mg/kg). This compound had a TD50 in the rotorod test of 278 mg/kg. Thus, the isopropyl derivative also is a highly potent anticonvulsant with a broad spectrum of action like α-EMTBL.

The amount of the anticonvulsant compound which would normally be administered is primarily dependent upon the physical characteristics of the recipient and the severity of the convulsant seizures. The amount to be administered must be an effective amount, that is, an amount which is medically beneficial but does not present toxic effects which overweigh the advantages which accompany its use. It would be expected that the adult human dosage would normally range upwardly from about 10 milligrams of the active compound. The preferable route of administration is orally in the form of capsules, tablets, syrups, elixers and the like, although parenteral administration also can be used. Suitable formulations of the active compound in pharmaceutically acceptable diluents and carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the disclosure herein without departing from the spirit and scope of the invention and it is intended that all such other examples be included with the scope of the appended claims.

What is claimed is:

1. An anticonvulsant compound having the following formula:

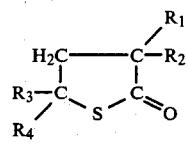

wherein
$R_1$ = alkyl or alkenyl having from 1 to about 4 carbon atoms,
$R_2$ = alkyl or alkenyl having from 1 to about 4 carbon atoms,
$R_3$ = H, alkyl or alkenyl having from 1 to about 4 carbon atoms,
$R_4$ = H, alkyl or alkenyl having from 1 to about 4 carbon atoms,
and in which $R_1$ and $R_2$ are dissimilar alkyl or alkenyl groups.

2. A compound of claim 1 in which $R_1$ and $R_2$ are alkyl and $R_3$ and $R_4$ are H.

3. α-ethyl-α-methyl-γ-thiobutyrolactone.

4. The method of preventing convulsant seizures in animals which comprises administering to such animals an effective amount of a compound having the formula:

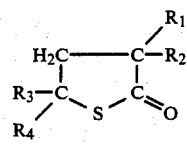

wherein
$R_1$ = H, alkyl or alkenyl having from 1 to about 4 carbon atoms,
$R_2$ = H, alkyl or alkenyl having from 1 to about 4 carbon atoms,
$R_3$ = H, alkyl or alkenyl having from 1 to about 4 carbon atoms,
$R_4$ = H, alkyl or alkenyl having from 1 to about 4 carbon atoms,
and in which at least one of $R_1$, $R_2$, $R_3$ or $R_4$ is not H.

5. The method of claim 4 in which $R_1$ and $R_2$ are alkyl and $R_3$ and $R_4$ are H.

6. The method of claim 4 in which the compound is α-ethyl-α-methyl-γ-thiobutyrolactone.

7. The method of claim 4 in which the compound is α-isopropyl-γ-thiobutyrolactone.

* * * * *